United States Patent [19]

Crain et al.

[11] Patent Number: 5,512,578
[45] Date of Patent: Apr. 30, 1996

[54] METHOD OF SIMULTANEOUSLY ENHANCING ANALGESIC POTENCY AND ATTENUATING DEPENDENCE LIABILITY CAUSED BY EXOGENOUS AND ENDOGENOUS OPIOD AGONISTS

[75] Inventors: Stanley M. Crain, Leonia, N.J.; Ke-Fei Shen, Flushing, N.Y.

[73] Assignee: Albert Einstein College of Medicine of Yeshiva University, a Division of Yeshiva University, Bronx, N.Y.

[21] Appl. No.: 276,966

[22] Filed: Jul. 19, 1994

Related U.S. Application Data

[63] Continuation-in-part of Ser. No. 97,460, Jul. 27, 1993, which is a continuation-in-part of Ser. No. 947,690, Sep. 19, 1992, abandoned.

[51] Int. Cl.⁶ .................................................. A61K 31/14
[52] U.S. Cl. ........................ 514/282; 514/811; 514/812
[58] Field of Search ............................ 514/282, 811, 514/812

[56] References Cited

U.S. PATENT DOCUMENTS

| | | | |
|---|---|---|---|
| 4,760,069 | 7/1988 | Rezeszotarski et al. | 514/285 |
| 4,889,860 | 12/1989 | Rezeszotarski et al. | 514/279 |
| 5,075,341 | 12/1991 | Mendelson et al. | 514/279 |
| 5,317,022 | 5/1994 | Borsodi et al. | 514/282 |
| 5,321,012 | 6/1994 | Mayer et al. | 514/25 |
| 5,352,680 | 10/1994 | Portoghese et al. | 514/282 |

FOREIGN PATENT DOCUMENTS

| | | | |
|---|---|---|---|
| 9406426 | 3/1994 | WIPO | 514/285 |

*Primary Examiner*—James H. Reamer
*Attorney, Agent, or Firm*—Amster, Rothstein & Ebenstein

[57] ABSTRACT

This invention relates to a method of selectively enhancing the analgesic potency of morphine and other clinically used bimodally-acting opioid agonists and simultaneously attenuating development of physical dependence, tolerance and other undesirable side effects caused by the chronic administration of said bimodally-acting opioid agonists comprising the co-administration of a bimodally-acting opioid agonist which activates both inhibitory and excitatory opioid receptor-mediated functions of neurons in the nociceptive (pain) pathways of the nervous system and an opioid receptor antagonist which selectively inactivates excitatory opioid receptor-mediated side effects. This invention also relates to a method of using excitatory opioid receptor antagonists alone to block the undesirable excitatory side effects of endogenous bimodally-acting opioid agonists which may be markedly elevated during chronic pain. This invention further relates to a method of long-term treatment of previously detoxified opiate, cocaine and alcohol addicts utilizing said excitatory opioid receptor antagonists, either alone or in combination with low-dose methadone, to prevent protracted physical dependence, and to compositions comprising an excitatory opioid receptor antagonist of the invention and a bimodally-acting opioid agonist.

32 Claims, 8 Drawing Sheets

Morphine

Naloxone

Naltrexone

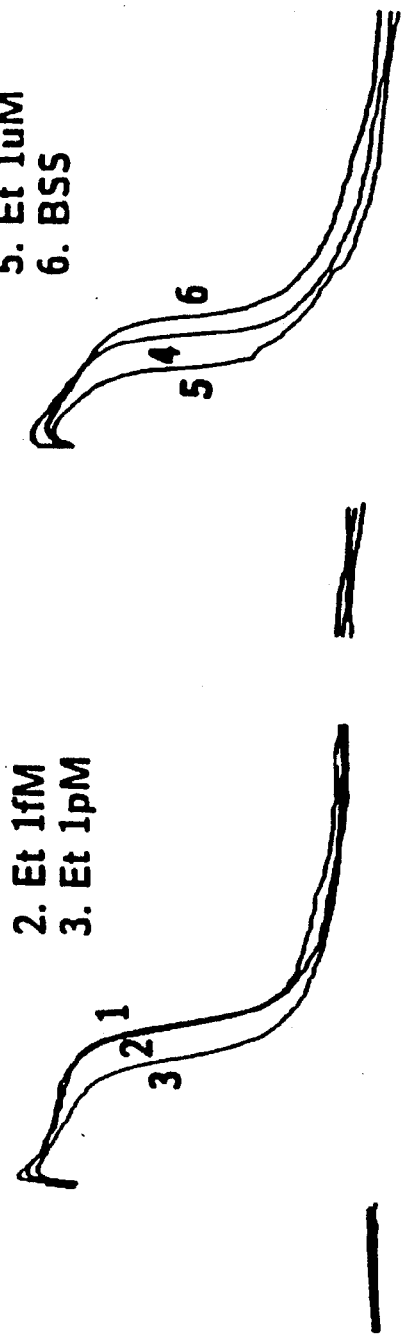
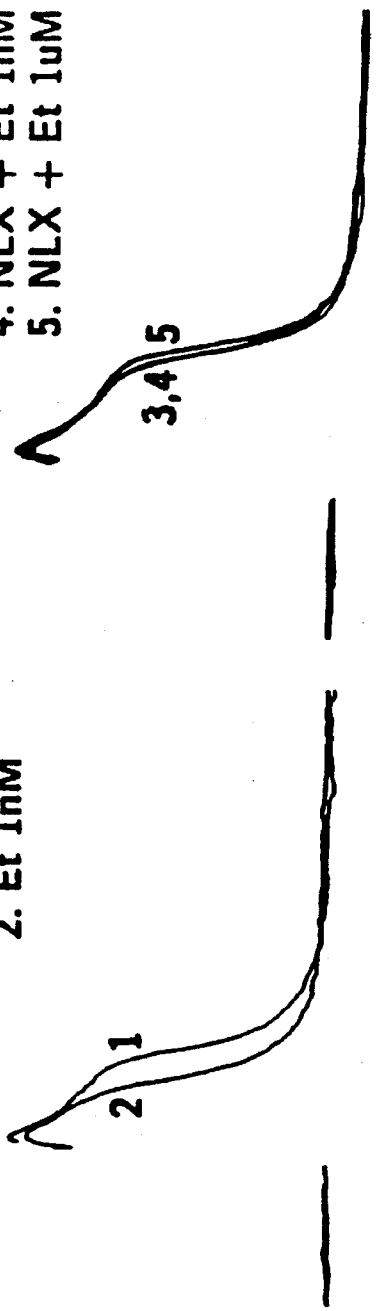
FIG. 2A
FIG. 2B

| Acute Test | Alteration of Action Potential Duration (APD) (APD shortening: ↓ ;APD prolongation: ↑ ;No APD change: 0) | | | |
|---|---|---|---|---|
| | Naive DRG Neurons | | Chronic Morphine–Treated Neurons (1uM; >1wk) After Washout with BSS | Chronic Co-treatment with Mor + Antag. at Excit. Op. Rec. (pM) |
| | Control BSS | BSS + Antag. at Excit.Op.Rec. (pM) | | |
| 1 – 10 uM morphine | ↓ (inhibitory) ("analgesia") | ↓↓ | ↑ ("tolerance") | ↓ |
| pM – nM morphine | ↑ ("excitatory antianalgesia") | ↓ (unmasking of inhibitory effects) | ↑ | ↓ |
| ~ fM morphine or dyn A–(1–13) | 0 | 0 | ↑ (excitatory supersensitivity) | 0 |
| nM naloxone | 0 | 0 | ↑ ("dependence") ("withdrawal effect") | 0 |

FIG. 6

METHOD OF SIMULTANEOUSLY ENHANCING ANALGESIC POTENCY AND ATTENUATING DEPENDENCE LIABILITY CAUSED BY EXOGENOUS AND ENDOGENOUS OPIOD AGONISTS

STATEMENT OF GOVERNMENT INTEREST

This invention was made with government support under NIDA research grant number DA 02031. As such, the government has certain rights in the invention.

CROSS-REFERENCE TO RELATED APPLICATIONS

This application is a Continuation-In-Part of application Ser. No. 08/097,460 filed Jul. 27, 1993, entitled METHOD OF SIMULTANEOUSLY ENHANCING ANALGESIC POTENCY AND ATTENUATING DEPENDENCE LIABILITY CAUSED BY MORPHINE AND OTHER OPIOID AGONISTS, currently pending, which is a Continuation-In-Part of application Ser. No. 07/947,690 filed Sep. 19, 1992, entitled A METHOD OF IDENTIFICATION OF NON-ADDICTIVE OPIOID ANALGESICS AND THE USE OF SAID ANALGESICS FOR TREATMENT OF OPIOID ADDICTION, now abandoned.

FIELD OF THE INVENTION

This invention relates to a method of enhancing the analgesic (inhibitory) effects of bimodally-acting opioid agonists, including morphine, codeine and other clinically used opioid analgesics, while at the same time attenuating anti-analgesic effects, physical dependence, tolerance, hyperexcitability, hyperalgesia, and other undesirable (excitatory) side effects typically caused by chronic use of bimodally-acting (excitatory and inhibitory) opioid agonists. As used herein, the term "opioid" refers to compounds which bind to specific opioid receptors and have agonist (activation) or antagonist (inactivation) effects at these receptors, such as opioid alkaloids, including the agonist morphine and the antagonist naloxone, and opioid peptides, including enkephalins, dynorphins and endorphins. As used herein, the term "opiate" refers to drugs derived from opium or related analogs.

In the instant invention, a very low dose of a selective excitatory opioid receptor antagonist is combined with a reduced dose of a bimodally-acting opioid agonist so as to enhance the degree of analgesia (inhibitory effects) and attenuate undesired side effects (excitatory effects). Opioid analgesia results from activation (by opioid agonists) of inhibitory opioid receptors on neurons in the nociceptive (pain) pathways of the peripheral and central nervous systems. The undesirable side effects, including anti-analgesic actions, hyperexcitability and hyperalgesia, the development of physical dependence, and some types of tolerance result from sustained activation (by bimodally-acting opioid agonists) of excitatory opioid receptors on neurons in the nociceptive (pain) pathways of the peripheral and central nervous systems. In addition, in the instant invention, long-term administration of ultra-low doses of the excitatory opioid receptor antagonists of the invention, either alone or in combination with low doses of conventional bimodally-acting opioid agonists, provides effective maintenance treatment of previously detoxified opiate, alcohol and cocaine addicts.

BACKGROUND OF THE INVENTION

Morphine or other bimodally-acting opioid agonists are administered to relieve severe pain due to the fact that they have analgesic effects mediated by their activation of inhibitory opioid receptors on nociceptive neurons (see North, *Trends Neurosci.*, Vol. 9, pp. 114–117 (1986) and Crain and Shen, *Trends Pharmacol. Sci.*, Vol. 11, pp. 77–81 (1990)). However, bimodally-acting opioid agonists also activate opioid excitatory receptors on nociceptive neurons, which attenuates the analgesic potency of the opioids and results in the development of physical dependence thereon and increased tolerance thereto (see Shen and Crain, *Brain Res.*, Vol. 597, pp. 74–83 (1992)), as well as hyperexcitability, hyperalgesia and other undesirable (excitatory) side effects. As a result, a long-standing need has existed to develop a method of both enhancing the analgesic (inhibitory) effects of bimodally-acting opioid agonists and limiting the undesirable (excitatory) side effects caused by such opioid agonists.

The grandparent Patent Application for the instant invention, Ser. No. 07/947,690, relates to a specific group of opioid agonists for use as low/non-addictive analgesics and for the treatment of opioid addiction. In the grandparent Application, it is stated that this group of opioid agonists bind to and activate inhibitory but not excitatory opioid receptors. In contrast, morphine and most other opioid alkaloids and peptides elicit bimodal effects by binding to and activating both excitatory and inhibitory opioid receptors.

To date, no method has been discovered or developed whereby two opioid compounds are co-administered, one of which binds to and acts as a selective agonist at inhibitory opioid receptors to cause analgesia and the other of which binds to and acts as a selective antagonist at excitatory opioid receptors so as to attenuate undesirable side effects caused by the administration of bimodally-acting opioid agonists while simultaneously enhancing the analgesic effects of said bimodally-acting opioid agonists.

It is therefore an object of this invention to provide a method of enhancing the analgesic potency of morphine and other bimodally-acting opioid agonists by blocking their anti-analgesic side effects.

It is a further object of this invention to provide a method of attenuating physical dependence, tolerance, hyperexcitability, hyperalgesia and other undesirable side effects caused by the chronic administration of bimodally-acting opioid agonists.

It is another object of this invention to provide a method for maintenance treatment of previously detoxified opiate, cocaine and alcohol addicts utilizing ultra-low doses of an excitatory opioid receptor antagonists, either alone or in combination with long-term administration of low doses of methadone.

It is yet another object of this invention to provide a composition which enhances the analgesic effects of bimodally-acting opioid agonists while simultaneously attenuating undesirable side effects caused by said opioid agonists, including physical dependence, tolerance, hyperexcitability and hyperalgesia.

It is still a further object of this invention to provide a composition which is useful for treatment of opiate, cocaine and alcohol addicts.

SUMMARY OF THE INVENTION

This invention is directed to a method of selectively enhancing the analgesic potency of morphine and other conventional bimodally-acting opioid agonists and simultaneously attenuating undesirable side effects, including physical dependence, caused by the chronic administration of said opioid agonists. Morphine and other bimodally-acting (inhibitory/excitatory) opioid agonists bind to and activate both inhibitory and excitatory opioid receptors on nociceptive neurons which mediate pain. Activation of inhibitory receptors by said agonists causes analgesia. Activation of excitatory receptors by said agonists results in anti-analgesic effects, hyperexcitability, hyperalgesia, as well as development of physical dependence and tolerance and other undesirable side effects. A series of antagonists which bind to excitatory opioid receptors (e.g., diprenorphine, naltrexone and naloxone) selectively block excitatory opioid receptor functions of nociceptive types of DRG neurons at 1,000 to 10,000-fold lower concentrations than are required to block inhibitory opioid receptor functions in these neurons. The co-administration of a bimodally-acting opioid agonist together with an ultra-low dose of an opioid antagonist which binds to and inactivates excitatory, but not inhibitory, opioid receptors results in the blocking of excitatory anti-analgesic side effects of said opioid agonists on these neurons, thereby resulting in enhanced analgesic potency. This enhanced analgesic potency permits the use of lower doses of morphine or other conventional opioid analgesics.

The preferred excitatory opioid receptor antagonists of the invention include naltrexone and naloxone, in addition to etorphine, dihydroetorphine, and diprenorphine which are disclosed in parent U.S. patent application Ser. No. 08/097, 460 and similarly acting opioid alkaloids and opioid peptides. Prior hereto, clinical uses of naloxone and naltrexone have been formulated to be administered at much higher doses (e.g. 50 mg), which block inhibitory opioid receptor functions mediating analgesia in addition to blocking excitatory opioid receptors. These high doses of antagonist are required as an antidote for acute opiate agonist overdose (e.g., respiratory depression). However, in the instant invention, long-term oral administration of ultra-low doses of naltrexone (for example about 1 µg) alone or in combination with low doses of methadone (e.g. mg) prevents protracted physical dependence which underlies resumption of drug abuse in previously detoxified opiate, cocaine and alcohol addicts. This is in contrast to clinical use of naltrexone prior hereto, wherein large (50 mg) tablets (Trexan) are administered, which produce dysphoria and other aversive side effects, and long-term treatment with high doses of methadone which results in physical dependence on methadone.

The opioid agonists of the invention include morphine or other bimodally-acting (inhibitory/excitatory) opioid alkaloids or opioid peptides that are in clinical use as analgesics, including codeine, fentanyl analogs, pentazocine, buprenorphine, methadone and endorphins.

Further, in chronic pain patients, the excitatory opioid receptor antagonists of the invention are administered alone in ultra-low doses to enhance the analgesic potency and decrease the dependence liability of endogenous (as opposed to exogenous) opioid peptides, including enkephalins, dynorphins and endorphins, so as to facilitate physiologic mechanisms which normally regulate opioid responsivity and nociceptive systems.

BRIEF DESCRIPTION OF THE DRAWINGS

The above brief description, as well as further objects and features of the present invention, will be more fully understood by reference to the following detailed description of the presently preferred, albeit illustrative, embodiments of the present invention when taken in conjunction with the accompanying drawings wherein:

FIG. 6 represents the assay procedure used to demonstrate that selective antagonists at excitatory opioid receptors prevent development of tolerance/dependence during chronic co-treatment of DRG neurons with morphine.

DETAILED DESCRIPTION OF THE INVENTION

Figure 1:
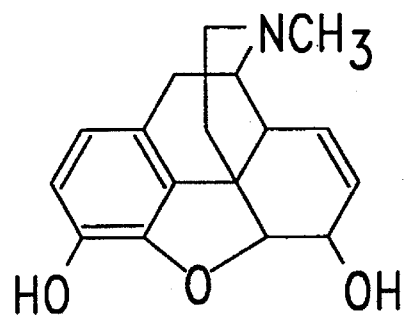
FIG. 1 represents the structural formulae of the bimodally-acting opioid agonist morphine and the preferred excitatory opioid receptor antagonists of the invention, naltrexone and naloxone. Naltrexone is the N-cyclopropylmethyl congener of naloxone.
Figure 1:
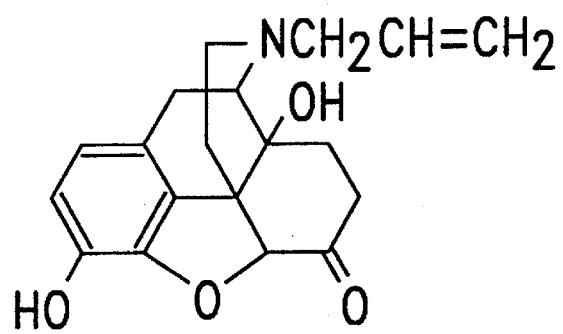
Figure 1:
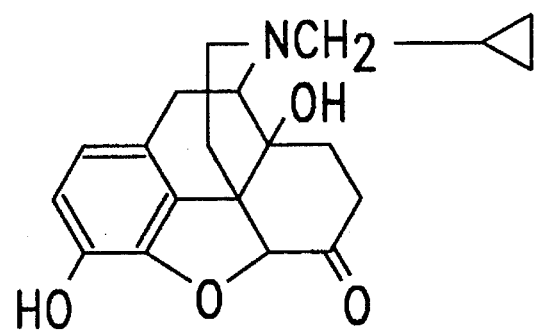

This invention is directed to a method of selectively enhancing the analgesic effect caused by the administration of a bimodally-acting opioid agonist and simultaneously attenuating undesirable side effects caused by the chronic administration of said bimodally-acting opioid agonists. This is performed by simultaneously inactivating excitatory opioid receptor-mediated functions of neurons in the nociceptive (pain) pathways and activating inhibitory opioid receptor-mediated mediated functions of nociceptive neurons. Low doses of a bimodally-acting opioid agonist and an excitatory opioid receptor antagonist are co-administered. The bimodally-acting opioid agonist binds to inhibitory receptors on nociceptive neurons so as to activate inhibitory opioid receptor-mediated functions, including analgesia, and concomitantly activates excitatory opioid receptors on nociceptive neurons. The excitatory opioid receptor antagonist binds to excitatory receptors on said neurons and thereby inactivates excitatory opioid receptor-mediated functions, including anti-analgesic effects, physical dependence and tolerance to the opioid agonist, hyperexcitability and hyperalgesia.

Alternatively, the excitatory opioid receptor antagonists of the invention can be used to pretreat patients prior to administering bimodally-acting exogenous opioids thereto, or used alone to enhance the analgesic potency and decrease the dependence liability of endogenous opioid peptides including enkephalins, dynorphins and endorphins, which are markedly unregulated in chronic pain patients.

In addition, this invention is directed to the use of said excitatory opioid receptor antagonists and opioid agonists for maintenance treatment of previously detoxified opiate addicts. Because addiction to cocaine and alcohol are also mediated by specific opioid-sensitive brain cell networks (see Gardner, et al. Substance Abuse 2 ed. pp. 70–99 (1992)), and because addiction to cocaine and alcohol are mediated by specific opioid-sensitive brain cell networks, the method of the invention for treating opiate addicts can also be used for the treatment of cocaine or alcohol addicts. Further, this invention is directed to a composition comprising an excitatory opioid receptor antagonist and a bimodally-acting opioid agonist.

The inventors have discovered that certain compounds act as excitatory opioid receptor antagonists, that is, they bind to and inactivate excitatory opioid receptors on neurons in the nociceptive pathways. The excitatory opioid receptor antagonists of the invention are preferably selected from the group consisting of naloxone, naltrexone, diprenorphine, etorphine and dihydroetorphine. One of the excitatory opioid receptor antagonists of the invention, naltrexone, can be administered orally at very low doses. For example, naltrexone can be administered at a level as low as 1 µg and will have selective antagonist action at excitatory, but not inhibitory, opioid receptors. All previous clinical use of naltrexone, as well as naloxone, has been at much higher (>mg) doses which results in antagonist actions at both inhibitory as well as excitatory opioid receptors. In addition, since the antagonists enhance the analgesic potency of the agonists, the agonists become effective when administered at markedly reduced doses which would otherwise be sub-analgesic.

The alkaloid opioid receptor antagonists of the invention inactivate mu, delta, kappa and other subtypes of excitatory opioid receptors. Etorphine and dihydroetorphine have very similar chemical structures and are potent analgesics which selectively activate inhibitory but not excitatory opioid receptors (see Shen and Crain, *Brain Res.*, Vol. 636, pp. 286–297 (1994)). Naltrexone, naloxone (see FIG. 1) and diprenorphine have slightly different chemical structures than etorphine and dihydroetorphine, which results in their acting as general opioid receptor antagonists at all types of inhibitory and excitatory opioid receptors (see Shen and Crain, *Brain Res.*, Vol. 491, pp. 227–242 (1989) and *Brain Res.*, Vol. 636, (1994)). Nevertheless, at very low (pM) concentrations, these compounds are all capable of selectively binding to and acting as antagonists at excitatory, but not inhibitory, opioid receptors on nociceptive DRG neurons.

The bimodally-acting opioid agonists of this invention preferably include morphine, codeine, methadone, pentazocine buprenorphine, fentanyl analogs, endorphins, and other opioid alkaloids and opioid peptides. Typically, the opioid agonists of the invention are mu, delta, kappa or epsilon opioid receptor agonists, and are capable of binding to inhibitory opioid receptors on neurons in the pain pathway. When these bimodally-acting agonists bind to inhibitory opioid receptors, they thereby activate inhibitory opioid receptor-mediated functions, including analgesia.

As discussed below, the inventors have discovered by studies of nociceptive DRG neurons that certain compounds (the excitatory opioid receptor antagonists of the invention), when used for pretreatment or when co-administered with bimodally-acting opioid agonists, are capable at very low dosages of enhancing the analgesic effects of the bimodally-acting opioid agonists at least 100–1000 fold by inactivating excitatory anti-analgesic side effects of said agonists. In addition, the excitatory opioid receptor antagonists of the invention prevent development of opioid tolerance and dependence which are mediated by sustained activation of excitatory opioid receptor functions.

In addition, the excitatory opioid receptor antagonists of the invention can be administered either alone or in conjunction with low, sub-analgesic doses of inhibitory opioid receptor agonists for long-term maintenance treatment of previously detoxified opiate, cocaine and alcohol addicts to prevent protracted physical dependence (see Goldberg, et al. (1969) and Crain, et al. (1992)), which underlies resumption of drug abuse.

The long-term treatment of detoxified addicts with selective antagonists blocks sustained activation of excitatory opioid receptor functions by endogenous opioid peptides. These peptides are present in the brain at concentrations that are well above the markedly reduced threshold required to activate chronic morphine-sensitized excitatory opioid receptors, thereby blocking the cellular mechanism proposed to underlie protracted physical dependence. Further, the excitatory opioid receptor antagonists can be administered alone to chronic pain patients to enhance the analgesic potency and decrease the dependence liability of endogenous opioid peptides, including enkephalins, dynorphins and endorphins which normally regulate nociceptive (pain) sensitivity and which are elevated during chronic pain.

Ordinarily, most conventional bimodally-acting opioid agonists are administered clinically in milligram dosages. By co-administering bimodally-acting opioid agonists with the excitatory opioid receptor antagonists of the invention, it is possible to achieve an analgesic effect with 10–100 times lower doses of the bimodally-acting opioid agonist than when said opioid agonist is administered alone. This is because the excitatory opioid receptor antagonists of the invention enhance the analgesic effects of the bimodally-acting opioid agonists by attenuating the anti-analgesic excitatory side effects of said opioid agonists. Hence, bimodally-acting opioid agonists which are administered with the excitatory opioid receptor antagonists of the invention are administered in an amount 10–100 times less than the amount of that bimodally-acting opioid agonist which has typically been administered for analgesia.

According to the present invention, the dose of excitatory opioid receptor antagonist to be administered is 100–1000 times less than the dose of bimodally-acting opioid agonist to be administered, for example, about 1 microgram of said antagonist together with 100–1000 micrograms of said agonist. These estimates of dosages are based on studies of nociceptive DRG neurons in culture. The excitatory opioid receptor antagonists, as well as the inhibitory opioid agonists, can be administered orally, sublingually, intramuscularly, subcutaneously or intravenously. Naltrexone is particularly useful since it can be administered orally at 1 µg doses, has long-lasting action and has been safely used in treatment of opiate addiction at 50 mg doses several times per week for several years (see Greenstein et al., *Subst. Abuse*, 2d ed. (1992) and Gonzales et al., *Drugs*, Vol. 35, pp. 192–213 (1988).

The co-administration of the opioid agonists and excitatory opioid receptor antagonists of the invention simultaneously activates inhibitory functions of nociceptive neurons mediating pain and inactivates excitatory functions of the same or other nociceptive neurons. In order to demonstrate this, electrophysiologic studies on the effects of opioids on nociceptive types of mouse sensory DRG neurons in tissue cultures were performed. It is shown below that this bimodal modulation is mediated by activating putative excitatory opioid receptors in addition to previously characterized inhibitory opioid receptors on sensory neurons.

It is shown that at low pM–nM concentrations, nearly all bimodally-acting opioids, including morphine, enkephalins, dynorphins, endorphins and specific mu, delta and kappa opioid agonists, elicit naloxone-reversible dose-dependent excitatory effects manifested by prolongation of the calcium-dependent component of the action potential duration (APD) of DRG neurons. In contrast, the same opioids generally elicit inhibitory APD shortening effects when applied at higher concentrations (0.1–1 µM).

The excitatory opioid effects on sensory neurons have been shown to be mediated by opioid receptors that are coupled via a cholera-toxin-sensitive stimulatory GTP-binding protein, Gs, to adenylate cyclase/cyclic AMP/protein kinase A-dependent ionic conductances that prolong the APD (resembling, for example, beta-adrenergic receptors). (See Crain and Shen, *Trends Pharmacol. Sci.*, Vol. 11, pp. 77–81 (1990)). On the other hand, inhibitory opioid effects are mediated by opioid receptors that are coupled via pertussis toxin-sensitive inhibitory G proteins: Gi to the adenylate cyclase/cyclic AMP system and Go to ionic conductances that shorten the APD (resembling, for example, alpha$_2$-adrenergic receptors). Shortening by opioids of the action potential of primary sensory neurons has generally been considered to be a useful model of their inhibition of calcium influx and transmitter release at presynaptic terminals in the dorsal spinal cord, thereby accounting for opioid-induced analgesia in vivo. (See North, *Trends Neurosci.*, Vol. 9, pp. 114–117 (1986) and Crain and Shen, *Trends Pharmacol. Sci.*, Vol. 11, pp. 77–81 (1990)).

Similarly, the delayed repolarization associated with the observed opioid-induced prolongation of action potential has been interpreted as evidence of excitatory effects of opioids on nociceptive types of sensory neurons (see Shen and Crain, *J. Neurosci.*, (1994, in press)) that may result in enhanced calcium influx and transmitter release at presynaptic terminals. This could account for some types of hyperalgesia and hyperexcitatory states elicited by opioids in vivo (see Crain and Shen, *Trends Pharmacol. Sci.*, Vol. 11, pp. 77–81 (1990); Shen and Crain, *Brain Res.*, Vol. 491, pp. 227–242 (1989); and Shen and Crain, *J. Neurosci.* (1994).

Chronic treatment of DRG neurons with typical bimodally-acting (excitatory/inhibitory) opioids (e.g., 1 µM D-ala$^2$-D-leu$^5$ enkephalin (DADLE) or morphine for 1 week) results in tolerance to the usual inhibitory APD-shortening effects of high concentrations of these opioids and supersensitivity to the excitatory APD-prolonging effects of these opioid agonists, as well as the opioid antagonist, naloxone (see Crain and Shen, *Brain Res.*, Vol. 575, pp. 13–24 (1992) and Shen and Crain, *Brain Res.*, Vol. 597, pp. 74–83 (1992)). It has been suggested that the latter electrophysiologic effects and related biochemical adaptations are cellular manifestations of physical dependence that may underlie some aspects of opiate addiction (see Shen and Crain, *Brain Res.*, Vol. 597, pp. 74–83 (1992) and Terwilliger et al., *Brain Res.*, Vol. 548, pp. 100–110 (1991)).

In contrast to bimodally-acting opioids, it has been discovered by the inventors that the opioid alkaloids etorphine (see Bentley and Hardy, *Proc. Chem. Soc.*, pp. 220 (1963) and Blane et al., *Brit. J. Pharmacol. Chemother.*, Vol. 30, pp. 11–22 (1967)) and dihydroetorphine (see Bentley and Hardy, *J. Amer. Chem. Soc.*, Vol. 89, pp. 3281–3286 (1967)) uniquely elicit dose-dependent, naloxone-reversible inhibitory effects on sensory neurons in DRG-spinal cord explants, even at concentrations as low as 1 pM, and show no excitatory effects at lower concentrations (see Shen and Crain, *Brain Res.*,, Vol. 636, pp. 286–297 (1994)). In addition, these potent inhibitory opioid receptor agonists also display unexpected antagonist effects at excitatory opioid receptors on DRG neurons. Acute pretreatment of DRG neurons with etorphine or dihydroetorphine, at low concentrations (<pM) which do not alter the APD, block the excitatory APD-prolonging effects of morphine and other bimodally-acting opioids and unmask inhibitory APD-shortening effects which normally require much higher concentrations. The potent inhibitory effect of etorphine and dihydroetorphine may be due to their selective activation of inhibitory opioid receptor-mediated functions while simultaneously inactivating excitatory opioid receptor-mediated functions in sensory neurons. In contrast, bimodally-acting opioids activate excitatory as well as inhibitory opioid receptors on DRG neurons, thereby decreasing the net inhibitory effectiveness of these agonists, resembling the attenuation of the inhibitory potency of systemic morphine by the "anti-analgesic" (excitatory) effect of dynorphin A release in spinal cord in mice (see Fujimoto et al., *Neuropharmacol.*, Vol. 29, pp. 609–617, (1990)).

The inventors have discovered that at ultra-low (pM) concentrations, naloxone and naltrexone act as selective antagonists at excitatory opioid receptors on DRG neurons, thereby unmasking potent inhibitory effects of bimodally-acting opioid agonists. At nM concentrations, naloxone blocks both inhibitory APD shortening in DRG neurons by µM opioid agonists as well as excitatory APD prolongation by pM–nM opioids. Systematic tests with lower concentrations of naloxone have revealed that pM naloxone acts selectively as an antagonist at excitatory opioid receptors. In DRG neurons where fM–nM morphine elicited dose-dependent excitatory APD prolongation, subsequent tests on the same neurons in the presence of 1 pM naloxone showed a complete block of opioid excitatory effects, and in some of the cells inhibitory APD shortening was evoked at these low (fM–nM) morphine concentrations. Similar unmasking of potent inhibitory effects of low concentrations of morphine was obtained in another series of DRG neurons tested with fM–nM morphine in the presence of pM naltrexone, whereas higher concentrations of naltrexone (nM–µM) blocked both inhibitory as well as excitatory opioid effects (see FIG. 5).

The selective antagonist action of ultra-low dose naloxone at excitatory opioid receptors is consonant with in vivo data where 0.1 fg of naloxone (i.t.) enhanced a type of behavioral (tail-flick) analgesia in mice shown to be mediated by an endogenous dynorphin A-(1–17) anti-analgesic system, whereas 100 fg of naloxone (i.t.) was required to significantly reduce analgesia mediated by direct i.t. injection of morphine or k opioid agonists (see Fujimoto et al., *J. Pharm. Exp. Ther.*, Vol. 251, pp. 1045–1052 (1989)).

Co-administration of low (pM) concentrations of etorphine during chronic treatment of DRG neurons with μM levels of morphine is effective in preventing development of the opioid excitatory supersensitivity and tolerance that generally occurs after sustained exposure to bimodally-acting opioids. Acute application of 1 fM dynorphin A(1–13) or 10 nM naloxone to DRG neurons chronically exposed to 3 μM morphine together with 1 pM etorphine (for greater than 1 week) did not evoke the usual excitatory APD prolongation observed in chronic morphine-treated cells, even when tested up to 6 hours after return to BSS. Furthermore, there was little or no evidence of tolerance to the inhibitory APD-shortening effects of μM morphine.

If etorphine was acting simply as an agonist at inhibitory opioid receptors, it might be predicted that the addition of 1 pM etorphine together with a $10^6$-fold higher concentration of morphine would have a negligible effect on chronic morphine-treated DRG neurons or would augment development of cellular signs of dependence. However, the results obtained are accounted for by the potent antagonist action of etorphine at excitatory opioid receptors during chronic morphine treatment, thereby preventing development of opioid excitatory supersensitivity and tolerance, just as occurs during chronic opioid treatment of DRG neurons in the presence of cholera toxin-B sub-unit (see Shen et al., *Brain Res.*, Vol. 575, pp. 13–24 (1992)), which selectively interferes with $GM_1$ ganglioside regulation of excitatory opioid receptor functions (see Shen et al., *Brain Res.*, Vol. 531, pp. 1–7 (1990) and Shen et al., *Brain Res.*, Vol. 559, pp. 130–138 (1991)).

Similarly, co-administration of ultra-low (pM) concentrations of naloxone or naltrexone during chronic treatment of DRG neurons with μM levels of morphine was effective in preventing development of the opioid excitatory supersensitivity and tolerance that generally occurs after sustained exposure to bimodally-acting opioids. Acute application of fM dynorphin A-(1–13) or fM morphine, as well as 1 nM naloxone to DRG neurons chronically exposed to 1 μM morphine together with 1 pM naloxone or naltrexone (for 1–10 weeks) did not evoke the usual excitatory APD prolongation observed in chronic morphine-treated cells (see Crain et al., (1992) and Shen et al., (1992)) tested after washout with BSS. Furthermore, there was no evidence of tolerance to the usual inhibitory effects of μM opioids.

Chronic co-treatment of nociceptive types of DRG neurons with morphine together with ultra-low (pM) concentrations of naltrexone or naloxone can therefore prevent the cellular manifestations of tolerance and dependence that generally occur in chronic morphine-treated DRG neurons. This data for naltrexone and naloxone on chronic morphine-treated nociceptive DRG neurons provides evidence that the formulation of opioid analgesic preparations comprising ultra-low doses of these excitatory opioid receptor antagonists and morphine (or codeine) will result in enhanced analgesic potency and low dependence liability.

The unmasking by pM naloxone or naltrexone of potent inhibitory (APD-shortening) effects of low pM–nM concentrations of morphine in DRG neurons accounts for the paradoxical enhancement by low-dose naloxone of: (1) morphine analgesia in humans (see Gillman et al., *Intern. J. Neurosci.*, Vol. 48, pp. 321–324 (1989); Gillman et al., *J. Nuerol. Sciences*, Vol. 49, pp. 41–49 (1981); and *South African J. Science* Vol. 83, pp. 560–563 (1987); (2) buprenorphine analgesia in humans and animals (see Pederson et al., *Brit. J. Anaesth.*, Vol. 57, pp. 1045–1046 (1985); Schmidt et al., *Anesthesia*, Vol. 40, pp. 583–586 (1985); and Bergman et al., *Arch. Int. Pharmacodyn.*, Vol. 291, pp. 229–237 (1988)); and (3) pentazocine analgesia in humans (see Levine et al., *J Clin, Invest.*, Vol. 82, pp. 1574–1577 (1988).

EXAMPLE 1

The effects of etorphine and dihydroetorphine on nociceptive types of DRG neurons in culture are described in Example 1. Etorphine and dihydroetorphine are the first compounds determined by the inventors by electrophysiologic analyses on DRG neurons to have specific antagonist action on excitatory opioid receptor functions when applied at ultra-low (pM) concentrations. This is in contrast to their well-known agonist action at inhibitory opioid receptors when applied at higher concentrations.

Etorphine and Dihydroetorphine Act as Potent Selective Antagonists at Excitatory Opioid Receptors on DRG Neurons Thereby Enhancing Inhibitory Effects of Bimodally-Acting Opioid Agonists Methods (Used in This and Following Examples): The experiments described herein were carried out on dorsal root ganglion (DRG) neurons in organotypic explants of spinal cord with attached DRGs from 13-day-old fetal mice after 3 to 5 weeks of maturation in culture. The DRG-cord explants were grown on collagen-coated coverslips in Maximow depression-slide chambers. The culture medium consisted of 65% Eagle's minimal essential medium, 25% fetal bovine serum, 10% chick embryo extract, 2 mM glutamine and 0.6% glucose. During the first week in vitro the medium was supplemented with nerve growth factor (NGF-7S) at a concentration of about 0.5 μg/ml, to enhance survival and growth of the fetal mouse DRG neurons.

In order to perform electrophysiologic procedures, the culture coverslip was transferred to a recording chamber containing about 1 ml of Hanks' balanced salt solution (BSS). The bath solution was supplemented with 4 mM $Ca^{2+}$ and 5 mM $Ba^{2+}$ (i.e., Ca,Ba/BSS) to provide a prominent baseline response for pharmacological tests. Intracellular recordings were obtained from DRG perikarya selected at random within the ganglion. The micropipettes were filled with 3M KCl (having a resistance of about 60–100 megohms) and were connected via a chloridized silver wire to a neutralized input capacity preamplifier (Axoclamp 2A) for current-clamp recording. After impalement of a DRG neuron, brief (2 msec) depolarizing current pulses were applied via the recording electrode to evoke action potentials at a frequency of 0.1 Hz. Recordings of the action potentials were stored on a floppy disc using the P-clamp program (Axon Instruments) in a microcomputer (IBM AT-compatible).

Drugs were applied by bath perfusion with a manually operated, push-pull syringe system at a rate of 2–3 ml/min. Perfusion of test agents was begun after the action potential and the resting potential of the neuron reached a stable condition during >4 minute pretest periods in control Ca, Ba/BSS. Opioid-mediated changes in the APD were considered significant if the APD alteration was >10% of the control value for the same cell and was maintained for the entire test period of 5 minutes. The APD was measured as the time between the peak of the APD and the inflection point on the repolarizing phase. The following drugs were used in this and the following Examples: etorphine, diprenorphine and morphine (gifts from Dr. Eric Simon); dihydroetorphine (gift from Dr. B.-Y. Qin, China and United Biomedical, Inc.); naloxone (Endo Labs); naltrexone, DADLE, dynorphin and other opioid peptides (Sigma).

Opioid alkaloids and peptides were generally prepared as 1 mM solutions in $H_2O$ and then carefully diluted with BSS to the desired concentrations, systematically discarding pipette tips after each successive 1–10 or 1–100 dilution step to ensure accuracy of extremely low (fM–pM) concentrations.

Results: Intracellular recordings were made from small- and medium-size DRG neuron perikarya (about 10–30 μm in diameter) which generate relatively long APDs (greater than 3 msec in Ca/Ba BSS) and which show characteristic responsiveness to opioid agonists and other properties of primary afferent nociceptive neurons as occur in vivo. Acute application of selective inhibitory opioid receptor agonists, e.g., etorphine, to these DRG neurons shortens the APD in 80–90% of the cells tested, whereas low concentrations of bimodally-acting (excitatory/inhibitory) opioids, e.g., morphine, dynorphin, enkephalins, prolong the APD in these same cells. Relatively small numbers of large DRG neurons (about 30–50 μm in diameter) survive in DRG-cord explants (about 10–20%) and show much shorter APDs (about 1–2 msec in Ca/Ba BSS), with no clear-cut inflection or "hump" on the falling phase of the spike. The APD of these large DRG neurons is not altered by exogenous opioids.

The opioid responsiveness of DRG neurons was analyzed by measuring the opioid-induced alterations in the APD of DRG perikarya. A total of 64 DRG neurons (from 23 DRG-cord explants) were studied for sensitivity to progressive increases in the concentration of etorphine (n=30) or dihydroetorphine (n=38). Etorphine rapidly and dose-dependently shortened the APD in progressively larger fractions of DRG cells at concentrations from 1 fM (30% of cells; n=26) to 1 μM (80% of cells; n=16) (see FIGS. 2 and 3).

Figure 2C:
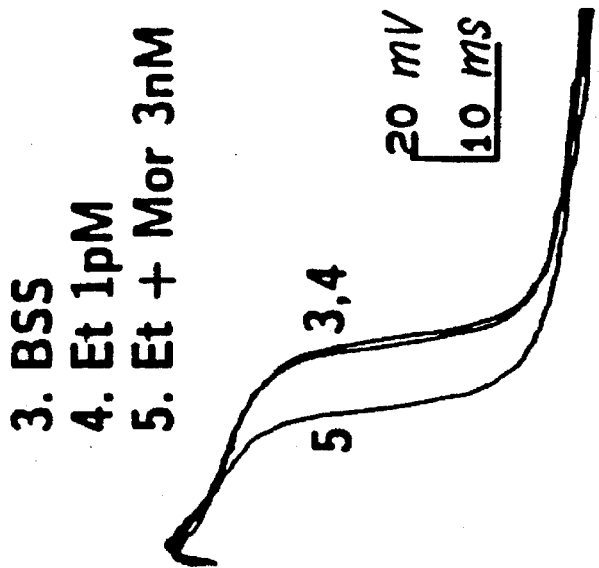
FIG. 2 represents the direct inhibitory effect of etorphine on the action potential duration (APD) of nociceptive types of sensory neurons and the blocking effect of etorphine on the excitatory response (APD prolongation) elicited by morphine. Acute application of low (pM-nM) concentrations of etorphine to naive dorsal root ganglion (DRG) neurons elicits dose-dependent, naloxone-reversible inhibitory shortening of the APD. In contrast, morphine and other bimodally-acting opioid agonists elicit excitatory APD prolongation at these low concentrations which can be selectively blocked by <pM levels of etorphine, resulting in unmasking of potent inhibitory APD shortening by nM morphine.
Figure 2C:
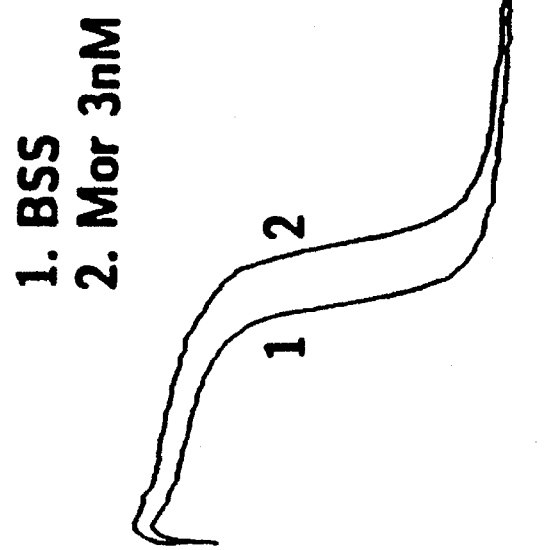

FIG. 2 shows that acute application of low (pM–nM) concentrations of etorphine to naive DRG neurons elicits dose-dependent, naloxone-reversible inhibitory shortening of the action potential duration (APD). In contrast, dynorphin (and many other bimodally-acting opioid agonists, e.g., morphine, DADLE) elicit excitatory APD prolongation at these low concentrations (see FIG. 3), which can be selectively blocked by < pM levels of etorphine, as well as by diprenorphine or naltrexone (see FIGS. 4 and 5). FIG. 2A record 1 shows the action potential (AP) generated by a DRG neuron in balanced salt solution containing 5 mM $Ca^{2+}$ and 5 mM $Ba^{2+}$ (BSS). AP response in this record (and in all records below) is evoked by a brief (2 msec) intracellular depolarizing current pulse. FIG. 2A records 2–5 show that APD is not altered by bath perfusion with 1 fM etorphine (Et) but is progressively shortened in 1 pM, 1 nM and 1 μM concentrations (5 minute test periods). FIG. 2A record 6 shows that APD returns to control value after transfer to BSS (9 minute test). FIG. 2B records 1 and 2 show that APD of another DRG neuron is shortened by application of 1 nM etorphine (2 minute test). FIG. 2B record 3 shows that APD returns to control value after transfer to 10 nM naloxone (NLX). FIG. 2B records 4 and 5 show that APD is no longer shortened by 1 nM or even 1 μM etorphine when co-perfused with 10 nM naloxone (5 minute test periods).

FIG. 2C records 1 and 2 show that APD of another DRG neuron is prolonged by application of 3 nM morphine. FIG. 2C record 3 shows that APD returns to control value by 5 minutes after washout. FIG. 2C record 4 shows that application of 1 pM etorphine does not alter the APD. FIG. 2C record 5 shows that APD is no longer prolonged by 3 nM morphine when co-perfused with 1 pM etorphine and instead is markedly shortened to a degree which would require a much higher morphine concentration in the absence of etorphine. Similar results were obtained by pretreatment with 1 pM diprenorphine (see FIG. 4), with 1 pM naltrexone (FIG. 5) or 1 pM naloxone. Records in this and subsequent Figures are from DRG neurons in organotypic DRG-spinal cord explants maintained for 3–4 weeks in culture.

Figure 3:
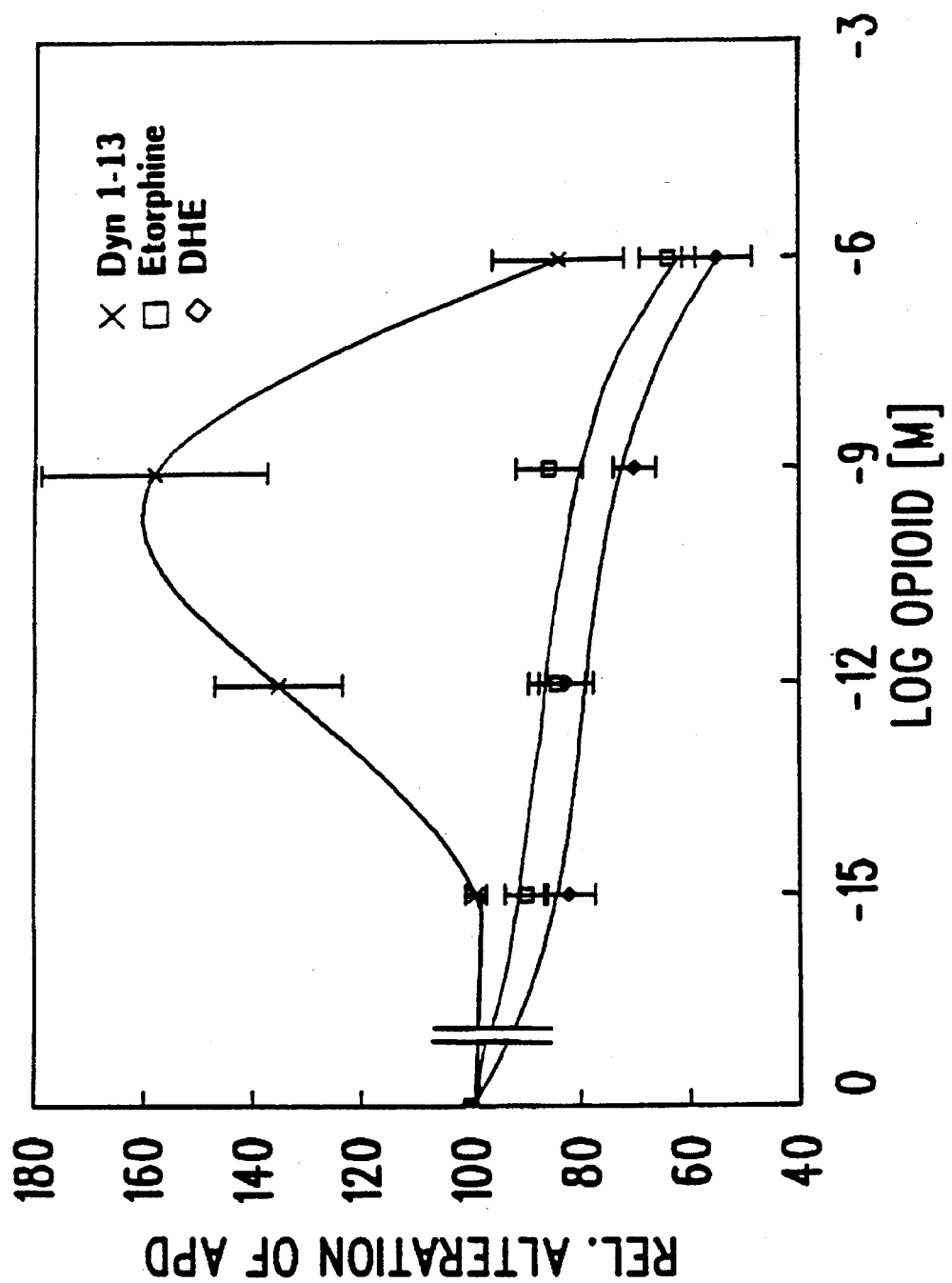
FIG. 3 represents dose-response curves of different opioids, showing that etorphine and dihydroetorphine elicit only inhibitory dose-dependent shortening of the APD of DRG neurons at all concentrations tested (fM–µM). In contrast, dynorphin A (as well as morphine and other bimodally-acting opioids) elicits dose-dependent excitatory APD prolongation at low concentrations (fM–nM) and requires much higher concentrations (about 0.1–1 µM) to shorten the APD, thereby resulting in-a bell-shaped dose-response curve.

FIG. 3 shows dose-response curves demonstrating that etorphine (Et) (□) and dihydroetorphine (DHE) (◇) elicit only inhibitory dose-dependent shortening of the APD of DRG neurons at all concentrations tested (fM–μM). In contrast, dynorphin A (1–13) (Dyn) (X) (as well as morphine and other bimodally-acting opioids) elicits dose-dependent excitatory APD prolongation at low concentrations (fM–nM) and generally requires much higher concentrations (about 0.1–1 μM) to shorten the APD, thereby resulting in a bell-shaped dose-response curve. Data were obtained from 11 neurons for the etorphine tests, 13 for the DHE tests and 35 for the dynorphin tests; 5, 8 and 9 neurons were tested (as in FIG. 2) with all four concentrations of etorphine, DHE and dynorphin, respectively (from fM to μM). For sequential dose-response data on the same neuron, the lowest concentrations (e.g., 1 fM) were applied first.

Dihydroetorphine was even more effective (n=38; FIG. 3). Naloxone (10 nM) prevented the etorphine- and dihydroetorphine-induced APD shortening which was previously elicited in the same cells (n=12; FIG. 2B). These potent inhibitory effects of etorphine and dihydroetorphine on DRG neurons at low concentrations are in sharp contrast to the excitatory APD-prolonging effects observed in similar tests with morphine and a wide variety of mu, delta and kappa opioids. None of the DRG neurons tested with different concentrations of etorphine or dihydroetorphine showed prominent APD prolongation.

The absence of excitatory APD-prolonging effects of etorphine and dihydroetorphine on DRG neurons could be due to low binding affinity of these opioid agonists to excitatory opioid receptors. Alternatively, these opioids might bind strongly to excitatory receptors, but fail to activate them, thereby functioning as antagonists. In order to distinguish between these two modes of action, DRG neurons were pretreated with etorphine at low concentrations (fM–pM) that evoked little or no alteration of the APD. Subsequent addition of nM concentrations of morphine, DAGO, DADLE or dynorphin to etorphine-treated cells no longer evoked the usual APD prolongation observed in the same cells prior to exposure to etorphine (n=11; see FIG. 2C). This etorphine-induced blockade of opioid excitatory effects on DRG neurons was often effective for periods up to 0.5–2 hours after washout (n=4).

These results demonstrate that etorphine, which has been considered to be a "universal" agonist at mu, delta and kappa opioid receptors (see Magnan et al., *Naunyn-Schmiedeberg's Arch. Pharmacol.*, Vol. 319, pp. 197–205 (1982)), has potent antagonist actions at mu, delta and kappa excitatory opioid receptors on DRG neurons, in addition to its well-known agonist effects at inhibitory opioid receptors. Pretreatment with dihydroetorphine (fM–pM) showed similar antagonist action at excitatory opioid receptor mediating nM opioid-induced APD prolongation (n=2). Furthermore, after selective blockade of opioid excitatory APD-prolonging effects by pretreating DRG neurons with low concentrations of etorphine (fM–pM), which showed little or no alteration of the APD, fM–nM levels of bimodally-acting opioids now showed potent inhibitory APD-shortening effects (5 out of 9 cells) (see FIG. 2C and FIG. 4). This is presumably due to unmasking of inhibitory opioid receptor-mediated functions in these cells after selective blockade of their excitatory opioid receptor functions by etorphine.

EXAMPLE 2

Diprenorphine, Naloxone and Naltrexone, at Low Concentrations, Show Potent Selective Antagonist Action at Excitatory Opioid Receptors Drug tests: Mouse DRG-cord explants, grown for >3 weeks as described in Example 1, were tested with the opioid antagonists, diprenorphine, naltrexone and naloxone. Electrophysiological recordings were made as in Example 1.

Results: The opioid receptor antagonists naloxone and diprenorphine were previously shown to block, at nM concentrations, both inhibitory APD shortening of DRG neurons by μM opioid agonists as well as excitatory APD prolongation by nM opioids. Tests at lower concentrations have revealed that pM diprenorphine, as well as pM naloxone or naltrexone, act selectively as antagonists at mu, delta and kappa excitatory opioid receptors, comparable to the antagonist effects of pM etorphine and dihydroetorphine. In the presence of pM diprenorphine, morphine (n=7) and DAGO (n=7) no longer elicited APD prolongation at low (pM–nM) concentrations (see FIG. 4A). Instead, they showed progressive dose-dependent APD shortening throughout the entire range of concentrations from fM to μM (see FIG. 4B), comparable to the dose-response curves for etorphine and dihydroetorphine (see FIG. 3 and FIG. 2C). This unmasking of inhibitory opioid receptor-mediated APD-shortening effects by pM diprenorphine occurred even in the presence of $10^6$-fold higher concentrations of morphine (see FIG. 4A, records 11 vs. 5).

Figure 4A:
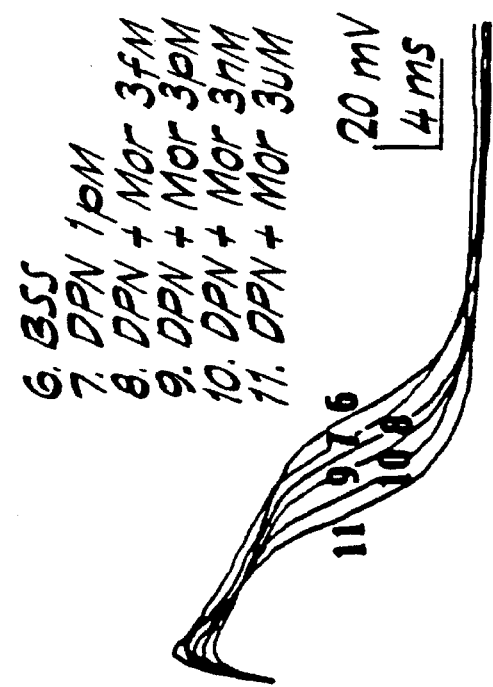
FIGS. 4A and 4B represent the selective blocking of excitatory APD-prolonging effects elicited by morphine in DRG neurons by co-administration of a low (pM) concentration of diprenorphine, thereby unmasking potent dose-dependent inhibitory APD shortening by low concentrations of morphine (comparable to the inhibitory potency of etorphine). In contrast, co-treatment with a higher (nM) concentration of DPN blocks both inhibitory as well as excitatory opioid effects.
Figure 4A:
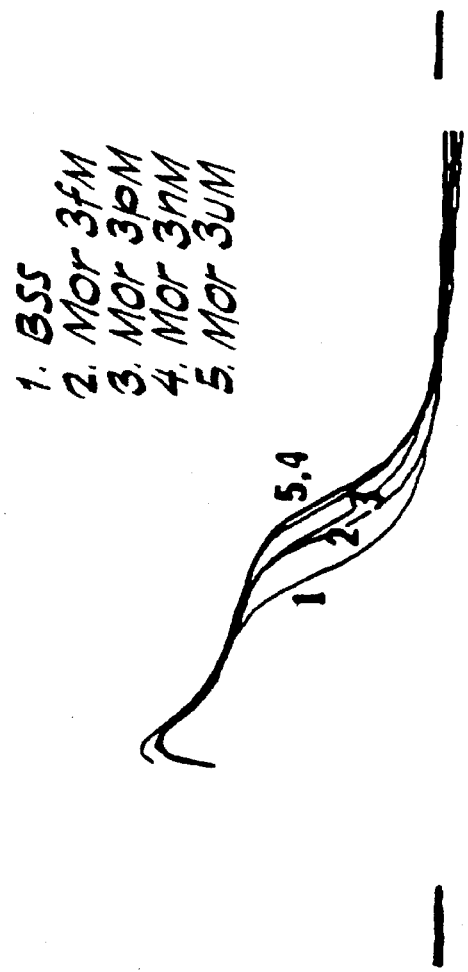
Figure 4B:
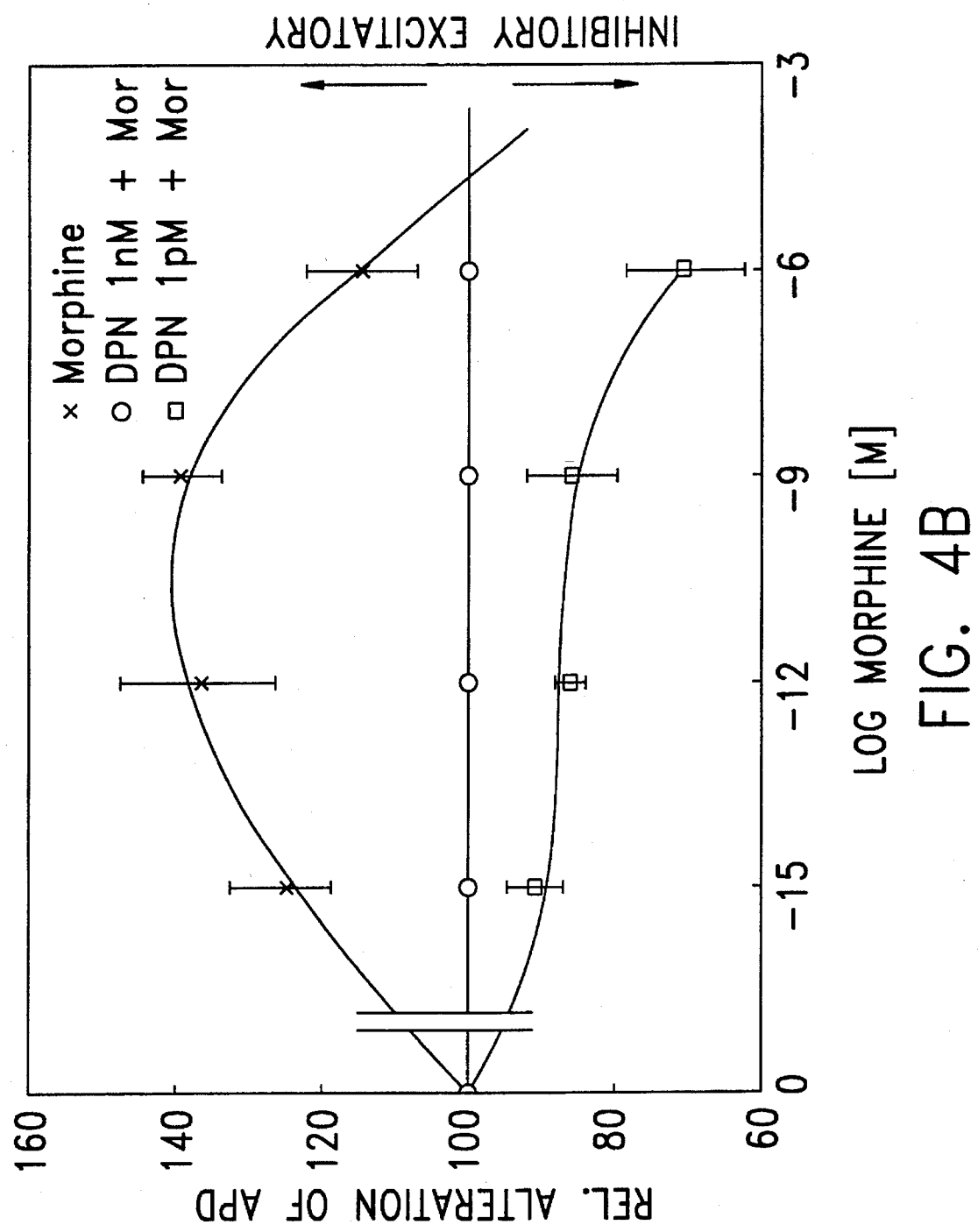

FIG. 4 shows that excitatory APD-prolonging effects elicited by morphine in DRG neurons are selectively blocked by co-administration of a low (pM) concentration of diprenorphine, thereby unmasking potent dose-dependent inhibitory APD shortening by low concentrations of morphine. FIG. 4A records 1–4 show that APD of a DRG neuron is progressively prolonged by sequential bath perfusions with 3 fM, 3 pM and 3 nM morphine (Mor). FIG. 4A record 5 shows that APD of this cell is only slightly shortened after increasing morphine concentration to 3 μM. FIG. 4A records 6 and 7 show that after transfer to BSS, the APD is slightly shortened during pretreatment for 17 minutes with 1 pM diprenorphine (DPN). FIG. 4A records 8–11 show that after the APD reached a stable value in DPN, sequential applications of 3 fM, 3 pM, 3 nM and 3 μM Mor progressively shorten the APD, in contrast to the marked APD prolongation evoked by these same concentrations of Mor in the absence of DPN (see also FIG. 2C). FIG. 4B dose-response curves demonstrate similar unmasking by 1 pM DPN of potent dose-dependent inhibitory APD shortening by morphine (□) in a group of DRG neurons (n=7), all of which showed only excitatory APD prolongation responses when tested prior to introduction of DPN (X). Note that the inhibitory potency of morphine in the presence of pM DPN becomes comparable to that of etorphine and dihydroetorphine (see FIG. 3). In contrast, pretreatment with a higher (nM) concentration of DPN blocks both inhibitory as well as excitatory effects of morphine (●).

Figure 5:
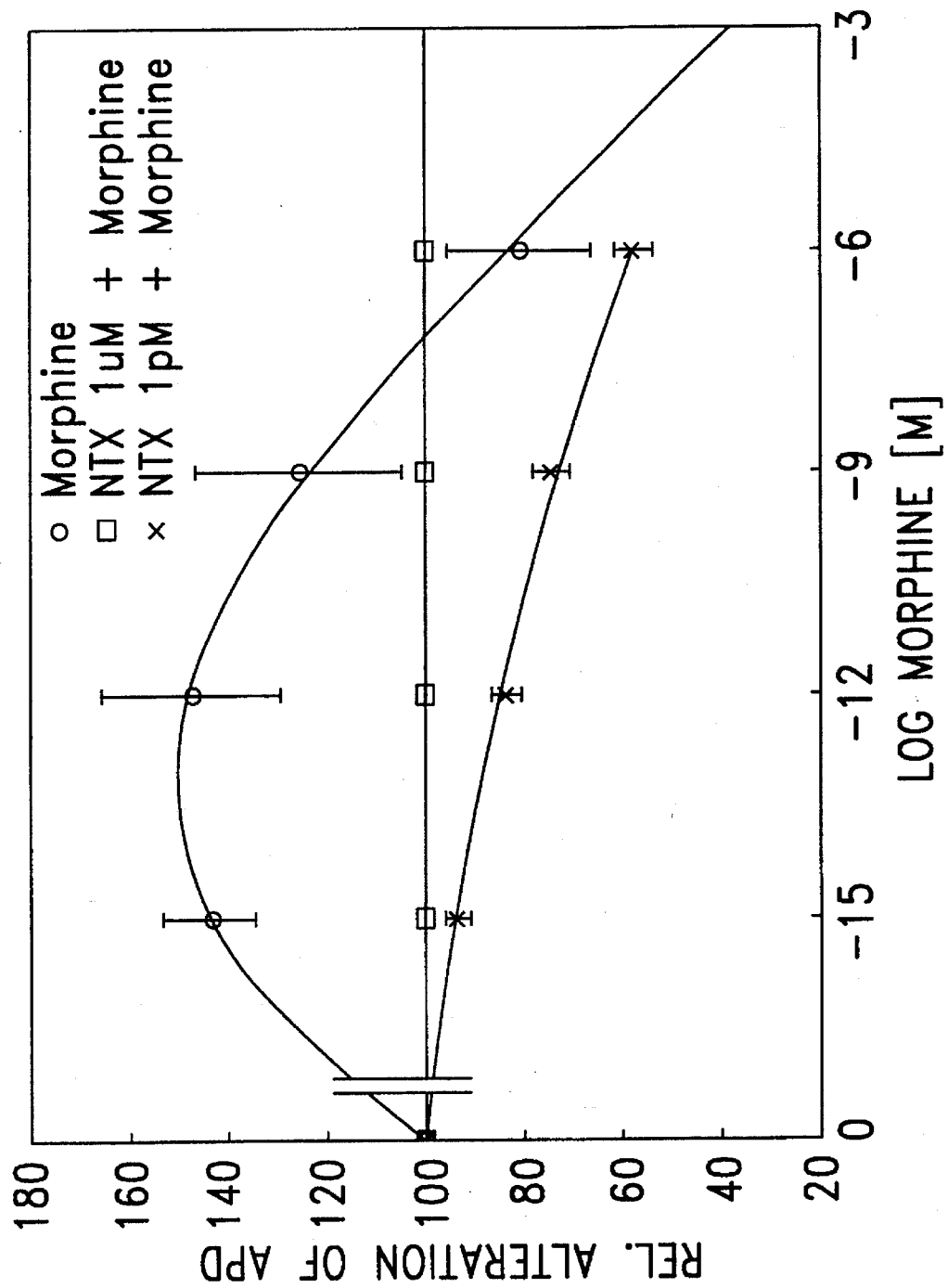
FIG. 5 represents similar selective blocking of excitatory APD-prolonging effects elicited by morphine in DRG neurons when co-administered with a low (pM) concentration of naltrexone, thereby unmasking potent inhibitory APD shortening by low concentrations of morphine. In contrast, a higher (µM) concentration of naltrexone blocks both inhibitory as well as excitatory opioid effects.

FIG. 5 shows that excitatory APD-prolonging effects elicited by morphine in DRG neurons (○) are also selectively blocked by co-administration of a low (pM) concentration of naltrexone (NTX), thereby unmasking potent dose-dependent inhibitory APD shortening by low concentrations or morphine (X). In contrast, pretreatment with a higher (μM) concentration of NTX blocks both inhibitory as well as excitatory effects of morphine (□) (similar blockade occurs with 1 nM NTX). These dose-response curves are based on data from 18 neurons, all of which showed only excitatory APD prolongation responses when tested prior to introduction of NTX. The inhibitory potency of morphine in the presence of pM NTX becomes comparable to that of etorphine and dihydroetorphine (see FIG. 3).

EXAMPLE 3

Chronic Co-treatment of DRG Neurons with Morphine and Ultra-low-dose Naloxone or Naltrexone Prevents Development of Opioid Excitatory Supersensitivity ("Dependence") and Tolerance Co-administration of ultra-low (pM) concentrations of naloxone or naltrexone during chronic treatment of DRG neurons with μM levels of morphine was effective in preventing development of opioid excitatory supersensitivity and tolerance which generally occurs after sustained exposure to bimodally-acting opioids. Acute application of fM dynorphin A-(1–13) or fM morphine (n=21), as well as 1 nM naloxone (n=11), to DRG neurons chronically exposed to 1 μM morphine together with 1 pM naloxone or naltrexone (for 1–10 weeks) did not evoke the usual excitatory APD prolongation observed in chronic morphine-treated cells tested after washout with BSS (see FIG. 6). Furthermore, there was no evidence of tolerance to the usual inhibitory effects of μM opioids (n=6) (FIG. 6).

These results are consonant with previous data that blockade of sustained opioid excitatory effects by cholera toxin-B sub-unit during chronic morphine treatment of DRG neurons prevents development of tolerance and dependence. (See Shen and Crain, *Brain Res.*, Vol. 597, pp. 74–83 (1992)). This toxin sub-unit selectively interferes with GM1 ganglioside regulation of excitatory opioid receptor functions (see Shen and Crain, *Brain Res.*, Vol. 531, pp. 1–7 (1990) and Shen et al., *Brain Res.*, Vol. 559, pp. 130–138 (1991)).

Similarly, in the presence of pM etorphine, chronic μM morphine-treated DRG neurons did not develop signs of tolerance or dependence. FIG. 6 outlines the assay procedure used for testing the effectiveness of these and other antagonists at excitatory opioid receptors in preventing development of tolerance/dependence during chronic co-treatment of DRG neurons with morphine.

Excitatory Opioid Receptor Antagonists Enhance Analgesic Potency and Reduce Dependence Liability and Other Side Effects of Morphine or Other Conventional Opioid Analgesics When Administered in Combination Electrophysiological studies on DRG neurons in culture indicated that pretreatment with low fM–pM concentrations of naltrexone, naloxone, diprenorphine, etorphine or dihydroetorphine is remarkably effective in blocking excitatory APD-prolonging effects of morphine or other bimodally-acting opioid agonists by selective antagonist actions at mu, delta and kappa excitatory opioid receptors on these cells. In the presence of these selective excitatory opioid receptor antagonists, morphine and other clinically used bimodally-acting opioid agonists showed markedly increased potency in evoking the inhibitory effects on the action potential of sensory neurons which are generally considered to underlie opioid analgesic action in vivo.

These bimodally-acting opioid agonists became effective in shortening, instead of prolonging, the APD at pM–nM (i.e., $10^{-12}$–$10^{-9}$M) concentrations, whereas 0.1–1 μM (i.e., $10^{-7}$–$10^{-6}$M) levels were generally required to shorten the APD (FIGS. 4B and 5). Selective blockade of the excitatory side effects of these bimodally-acting opioid agonists eliminates the attenuation of their inhibitory effectiveness that would otherwise occur. Hence, according to this invention, the combined use of a relatively low dose of one of these selective excitatory opioid receptor antagonists, together with morphine or other bimodally-acting mu, delta or kappa opioid agonists, will markedly enhance the analgesic potency of said opioid agonist, and render said opioid agonist comparable in potency to etorphine or dihydroetorphine, which, when used alone at higher doses, are >1000 times more potent than morphine in eliciting analgesia.

Co-administration of one of these excitatory opioid receptor antagonists at low (pM) concentration ($10^{-12}$M) during chronic treatment of sensory neurons with $10^{-6}$M morphine or other bimodally-acting opioid agonists (>1 week in culture) prevented development of the opioid excitatory supersensitivity, including naloxone-precipitated APD-prolongation, as well as the tolerance to opioid inhibitory effects that generally occurs after chronic opioid exposure. This experimental paradigm was previously utilized by the inventors on sensory neurons in culture to demonstrate that co-administration of $10^{-7}$M cholera toxin-B sub-unit, which binds selectively to GM1 ganglioside and thereby blocks excitatory GM1-regulated opioid receptor-mediated effects, but not opioid inhibitory effects (see Shen and Crain, *Brain Res.*, Vol. 531, pp. 1–7 (1990)), during chronic opioid treatment prevents development of these plastic changes in neuronal sensitivity that are considered to be cellular manifestations related to opioid dependence/addiction and tolerance in vivo (see Shen and Crain, *Brain Res.*, Vol. 597, pp. 74–83 (1992)).

Hence, according to this invention, the sustained use of a relatively low clinical dose of one of these selective excitatory opioid receptor antagonists, e.g., about 1 microgram of naltrexone, naloxone, etorphine, dihydroetorphine or diprenorphine, in combination with 100–1000 micrograms of morphine or other conventional bimodally-acting opioid analgesics will result in analgesia comparable to that elicited by said analgesics when administered alone in >10 milligram doses and will attenuate or even prevent development of tolerance, physical dependence and other undesirable excitatory side effects generally associated with said analgesics. Furthermore, administration of μg doses of these excitatory opioid receptor antagonists alone will enhance the analgesic effects of endogenous opioid peptides and thereby decrease chronic pain.

Treatment of Detoxified Opiate Addicts

Long-term maintenance treatment of previously detoxified opiate, cocaine and alcohol addicts to prevent protracted dependence is carried out by long-term oral administration of ultra-low doses (about 1 μg) of naltrexone. Ultra-low dose naltrexone selectively blocks resumption of the sustained activation of excitatory opioid receptor functions that are required for the development of protracted opioid dependence as well as opioid-mediated cocaine and alcohol dependence without inducing dysphoria or other adverse side effects caused by high-dose naltrexone blockade of inhibitory opioid receptor functions. Alternatively, ultra-low dose (about 1 μg) naltrexone can be administered long-term in combination with low-dose methadone to provide effective treatment for addiction.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

We claim:

1. A method for selectively enhancing the analgesic potency of a bimodally-acting opioid agonist and simultaneously attenuating anti-analgesia, hyperalgesia, hyperexcitability, physical dependence and/or tolerance effects associated with the administration of said bimodally-acting opioid agonist, comprising administering to a subject an analgesic or sub-analgesic amount of said bimodally-acting opioid agonist and an amount of an excitatory opioid receptor antagonist effective to enhance the analgesic potency of said bimodally-acting opioid agonist and attenuate the anti-analgesia, hyperalgesia, hyperexcitability, physical dependence and/or tolerance effects of said bimodally-acting opioid agonist.

2. The method of claim 1 wherein the excitatory opioid receptor antagonist is selected from the group consisting of naltrexone, naloxone, etorphine, diprenorphine, dihydroetorphine, and similarly acting opioid alkaloids and opioid peptides.

3. The method of claim 1 wherein the bimodally-acting opioid agonist is selected from the group consisting of morphine, codeine, fentanyl analogs, pentazocine, buprenorphine, methadone, enkephalins, dynorphins, endorphins and similarly acting opioid alkaloids and opioid peptides.

4. The method of claim 1 wherein the amount of the excitatory opioid receptor antagonist administered is at least 100–1000 fold less than the amount of the bimodally-acting opioid agonist administered.

5. The method of claim 2 wherein the excitatory opioid receptor antagonist is naltrexone.

6. The method of claim 3 wherein the bimodally-acting opioid agonist is morphine.

7. The method of claim 3 wherein the bimodally-acting opioid agonist is codeine.

8. The method of claim 1 wherein the mode of administration is selected from the group consisting of oral, sublingual, intramuscular, subcutaneous and intravenous.

9. The method of claim 1 wherein the opioid receptor antagonist is naltrexone, and is administered orally.

10. A method for treating a detoxified opiate, cocaine or alcohol addict so as to prevent protracted dependence thereon comprising administering to the detoxified addict over a long term an amount of an excitatory opioid receptor antagonist which does not block but instead enhances the analgesic effect of morphine and other bimodally-acting opioid agonists.

11. The method of claim 10 wherein the antagonist is administered in combination with a sub-analgesic amount of a long-lasting bimodally-acting opioid agonist.

12. The method of claim 11 wherein the opioid agonist is methadone.

13. The method of claim 10 wherein the excitatory opioid receptor antagonist is selected from the group consisting of naloxone, naltrexone, etorphine, dihydroetorphine, diprenorphine, and similarly acting opioid alkaloids and opioid peptides.

14. The method of claim 13 wherein the excitatory opioid receptor antagonist is naltrexone.

15. The method of claim 11 wherein the bimodally-acting opioid agonist is methadone and the excitatory opioid receptor antagonist is naltrexone.

16. A composition comprising an analgesic or sub-analgesic amount of a bimodally-acting opioid agonist and an amount of an excitatory opioid receptor antagonist effective to enhance the analgesic potency of said bimodally-acting opioid agonist and attenuate the anti-analgesia, hyperalgesia, hyperexcitability, physical dependence and/or tolerance effects of said bimodally-acting opioid agonist.

17. The composition of claim 16 wherein the excitatory opioid receptor antagonist is selected from the group consisting of naltrexone, naloxone, etorphine, diprenorphine, dihydroetorphine, and similarly acting opioid alkaloids and opioid peptides.

18. The composition of claim 16 wherein the bimodally-acting opioid agonist is selected from the group consisting of morphine, codeine, fentanyl analogs, pentazocine, methadone, buprenorphine, enkephalins, dynorphins, endorphins and similarly acting opioid alkaloids and opioid peptides.

19. The method of claim 1 wherein the bimodally-acting opioid agonist is morphine and the excitatory opioid receptor antagonist is naltrexone.

20. The method of claim 3 wherein the bimodally-acting opioid agonist is methadone.

21. The composition of claim 16 wherein the amount of the excitatory opioid receptor antagonist is at least 100–1000 fold less than the amount of the bimodally-acting opioid agonist.

22. The composition of claim 17 wherein the excitatory opioid receptor antagonist is naltrexone.

23. The composition of claim 18 wherein the bimodally-acting opioid agonist is morphine.

24. The composition of claim 18 wherein the bimodally-acting opioid agonist is methadone.

25. The composition of claim 16 wherein the bimodally-acting opioid agonist is morphine and the excitatory opioid receptor antagonist is naltrexone.

26. A method for treating pain in a subject comprising administering to said subject an analgesic or sub-analgesic amount of a bimodally-acting opioid agonist and an amount of an excitatory opioid receptor antagonist effective to enhance the analgesic potency of said bimodally-acting opioid agonist and attenuate the anti-analgesia, hyperalgesia, hyperexcitability, physical dependence and/or tolerance effects of said bimodally-acting opioid agonist.

27. The method of claim 26 wherein the bimodally-acting opioid agonist is selected from the group consisting of morphine, codeine, fentanyl analogs, pentazocine, methadone, buprenorphine, enkephalins, dynorphins, endorphins and similarly acting opioid alkaloids and opioid peptides.

28. The method of claim 26 wherein the excitatory opioid receptor antagonist is selected from the group consisting of naltrexone, naloxone, etorphine, diprenorphine and dihydroetorphine, and similarly acting opioid alkaloids and opioid peptides.

29. The method of claim 26 wherein amount of the excitatory opioid receptor antagonist administered is at least 100–1000 fold less than the amount of the bimodally-acting opioid agonist administered.

30. The method of claim 26 wherein the excitatory opioid receptor antagonist is naltrexone.

31. The method of claim 26 wherein the bimodally-acting opioid receptor agonist is morphine.

32. The method of claim 26 wherein the bimodally-acting opioid agonist is morphine and the excitatory opioid receptor antagonist is naltrexone.

* * * * *